(12) United States Patent
Thompson

(10) Patent No.: US 8,584,291 B2
(45) Date of Patent: Nov. 19, 2013

(54) WHOLE MOUTH TOOTHBRUSH

(76) Inventor: Garey Thompson, Corte Madera, CA (US)

(*) Notice: Subject to any disclaimer, the term of this patent is extended or adjusted under 35 U.S.C. 154(b) by 163 days.

(21) Appl. No.: 13/066,529

(22) Filed: Apr. 18, 2011

(65) Prior Publication Data

US 2012/0260442 A1    Oct. 18, 2012

(51) Int. Cl.
*A46B 13/02*    (2006.01)

(52) U.S. Cl.
USPC ................................. 15/22.1; 15/23

(58) Field of Classification Search
USPC ............... 15/22.1, 22.3, 23, 24, 28, 167.2
See application file for complete search history.

(56) References Cited

U.S. PATENT DOCUMENTS

| | | | | |
|---|---|---|---|---|
| 4,538,315 A | * | 9/1985 | Barth | 15/23 |
| 5,177,827 A | * | 1/1993 | Ellison | 15/22.1 |
| 5,337,435 A | * | 8/1994 | Krasner et al. | 15/23 |
| 6,955,539 B2 | * | 10/2005 | Shortt et al. | 433/118 |

* cited by examiner

*Primary Examiner* — Robert Scruggs
(74) *Attorney, Agent, or Firm* — Henry J. Recla

(57) ABSTRACT

A whole mouth toothbrush with an elongate hollow handle portion, and attached U shaped brush retaining portion. The housing holds an electric motor, a battery power supply, a microprocessor, a printed circuit board and an on-off switch. A primary drive belt connects the motor shaft to a first brush spindle. A plurality of secondary drive belts connect the first brush spindle to the remaining brush spindles. Each spindle terminates in a rotating brush head. Upper brush heads brush the user's top teeth and the lower spindles brush the user's bottom teeth. The microprocessor is programmed to cause the brush retaining shafts to cycle back and forth from a clockwise rotation to a counter clockwise rotation.

10 Claims, 5 Drawing Sheets

WHOLE MOUTH TOOTHBRUSH

CROSS REFERENCE TO RELATED APPLICATIONS

Not Applicable

STATEMENT REGARDING FEDERALLY SPONSORED RESEARCH OR DEVELOPMENT

Not Applicable

DESCRIPTION OF ATTACHED APPENDIX

Not Applicable

BACKGROUND OF THE INVENTION

This invention relates generally to the field of toothbrush devices and more specifically to a whole mouth toothbrush.

People of all ages and manual dexterity levels need to brush their teeth on a daily basis to keep their teeth clean and help prevent tooth decay. Some people, such as the elderly and the physically challenged, have a hard time holding a traditional toothbrush handle in all the various positions necessary for reaching all the portions of the user's mouth and teeth.

To this end, some inventors have proposed toothbrush designs that can brush all the user's teeth at a single time while the user holds the brush handle in one central position. For example, Terry Solow, in his U.S. Pat. No. 4,224,710 discloses a U shaped toothbrush having bristles that can manually brush all sides of the user's teeth. In a second patent, Benedict Ellison, in his U.S. Pat. No. 5,177,827 discloses a battery powered U shaped toothbrush that attempts to brush all portions of the user's teeth at once.

However there are deficiencies in the prior technology. The Solow design is a manual device that requires the user to move their teeth up and down to brush them. This type of action does not provide the most effective brushing technique. The Ellison patent describes a motorized toothbrush where a number of long brushes are bent into partial U shapes and rotated. Although this design might provide adequate cleaning power, it is questionable whether this design can actually be put into practice since it is requiring the brushes to both bend and rotate at the same time.

BRIEF SUMMARY OF THE INVENTION

The primary object of the invention is to provide an electric toothbrush that can brush all the teeth in a user's mouth at the same time.

Another object of the invention is to provide an electric toothbrush that protects the user's cheeks from bristle contact.

Another object of the invention is to provide an electric toothbrush that can brush the tops of molar teeth as well as the sides of all other teeth.

A further object of the invention is to provide an electric toothbrush that includes the ability to alternate direction of bristle rotation.

Other objects and advantages of the present invention will become apparent from the following descriptions, taken in connection with the accompanying drawings, wherein, by way of illustration and example, an embodiment of the present invention is disclosed.

In accordance with a preferred embodiment of the invention, there is disclosed a whole mouth toothbrush comprising: an elongate hollow handle portion, a U shaped brush retaining portion, an electric motor, a battery power supply, a microprocessor, a printed circuit board, an on-off switch, a primary drive belt, a plurality of secondary drive belts, a plurality of brush heads, a plurality of brush retaining spindle shafts, a first embodiment of said brush retaining spindles capable of retaining an upper bristle head and a lower bristle head for the purpose of cleaning the side portions of the user's teeth, a second embodiment of said brush retaining spindles capable of retaining an upper bristle head and a lower bristle head for the purpose of cleaning the top molar portions of the user's teeth, said brush retaining spindles also having a fixedly and centrally located first and second belt retaining pulleys, said motor, said battery power supply, said microprocessor, said printed circuit board and said primary drive belt all housed within said hollow elongate handle, said primary drive belt rotatably attached to said motor shaft on one end and to a first brush retaining spindle on the opposite end, said U shaped brush retaining portion including a centrally disposed hollow U shaped housing surrounded by an outer U shaped wall, said U shaped hollow housing retaining within it said first and second belt retaining pulleys of said brush retaining spindles, said spindle shafts each exiting upper and lower apertures located on the top and bottom surface of said U shaped hollow housing, said brush heads fixedly attached to the exposed upper and lower said spindle shafts, said first embodiment of said brush retaining spindles and attached brush heads mounted near the outer perimeter and inner perimeter of said U shaped hollow housing for the purpose of cleaning the inside surface and outside surfaces of the user's teeth, said second embodiment of said brush retaining spindles and attached brush heads mounted at the central portion of the top and bottom surface of said U shaped hollow housing for the purpose of cleaning the flat molar surfaces of the user's teeth, said secondary drive belts rotatably attached at one end to the first said belt retaining pulley of said first brush retaining spindle and the remaining secondary drive belts attached in a daisy chain fashion from the second belt retaining pulley of said first brush retaining spindle to the remaining said spindle pulleys so that when said first pulley spindle is caused to rotate, all remaining pulley spindles also rotate, said U shaped brush retaining portion also including upwardly and downwardly extended outer walls which are fixedly attached to the outer perimeter of said U shaped housing and which protect the user's cheeks from said rotating bristles, said on-off switch having an actuation button that protrudes from an aperture located on the said elongate hollow handle portion, said battery power supply providing power to said motor when said on-off switch is pressed, said microprocessor mounted to said printed circuit board, and said microprocessor programmed to cause said brush retaining shafts to cycle back and forth from a clockwise rotation to a counter clockwise rotation.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Figure 1:
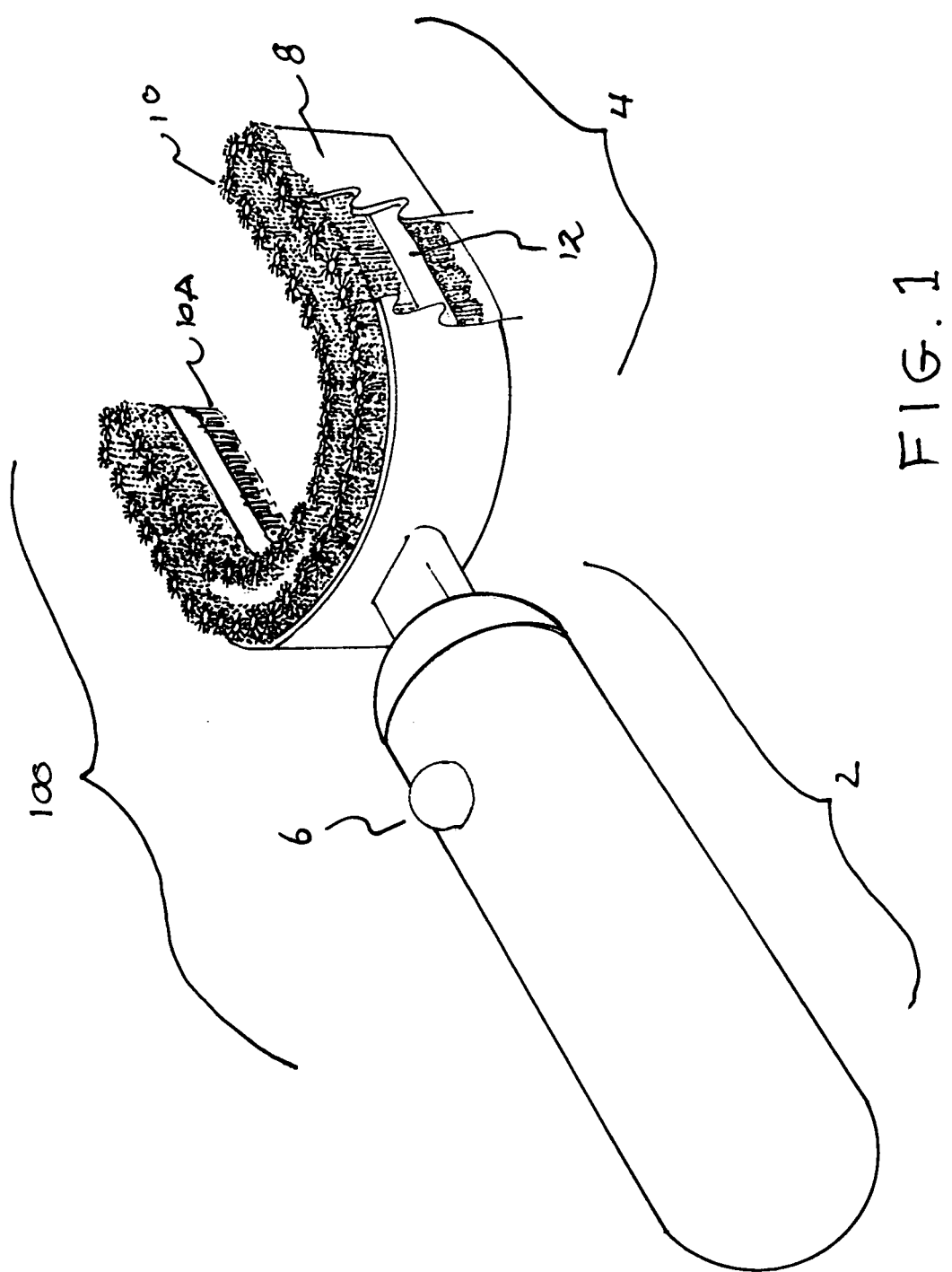
FIG. 1 is a perspective view of the invention.

Referring now to FIG. 1 we see a perspective view of the whole mouth toothbrush of the present invention 100

The invention is comprised of an elongate hollow housing 2 and a U shaped brush retaining portion 4. The bristles 10, 10A are positioned to brush all the teeth in the user's mouth at one time. The user simply has to hold onto the handle portion 2 and press the on-off button 6 which causes the bristles to rotate and thereby clean the user's teeth. A U shaped hollow housing 12 contains brush spindles 26 as will be described below. The upper brush heads 10 and the lower brush heads 10A are attached to the spindles 26. An outer wall 8 is attached to the outside perimeter of the hollow U shaped housing 12 and protects the user's cheeks from being affected by the bristles 10, 10A.

Figure 2:
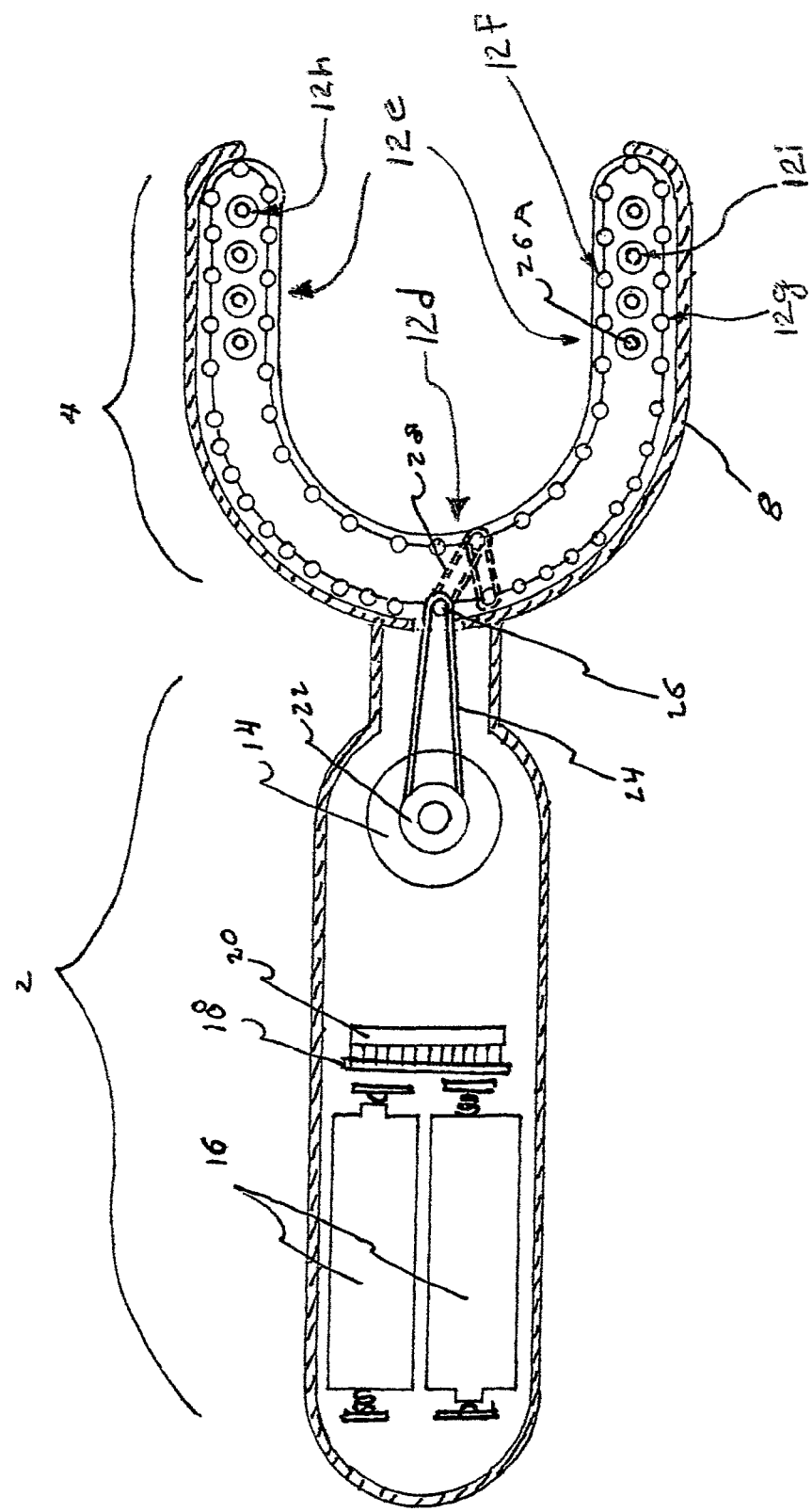
FIG. 2 is a section view longitudinally bisecting the invention.

FIG. 2 shows a longitudinal section view of the invention 100. The hollow handle portion 2 containers a battery power supply 16, a printed circuit board 18, a microprocessor 20 and an electric motor 14. When the user presses the on-off button, the motor shaft and attached pulley 22 rotate causing primary drive belt 24 to rotated spindle shaft 26. Secondary drive belts 28, 28A transfer rotational power to the remaining spindle shafts 26 in a daisy chain fashion as can be seen clearly in the partial section view of FIG. 4. For additional traction, the drive belts 24, 28 can be in the form of miniature timing belts, and the shaft spindles 26 can include a belt mating architecture. Microprocessor 20 is mounted to printed circuit board 18 and is programmed to cause the motor to rotate in a clockwise rotation for a few seconds, and then rotate in a counter-clockwise rotation for a few seconds. This cycle continues as long as the brush 100 is in operation. The alternation of rotation helps remove debris between teeth and cleans the teeth more completely than continuous rotation in one direction.

Figure 3:
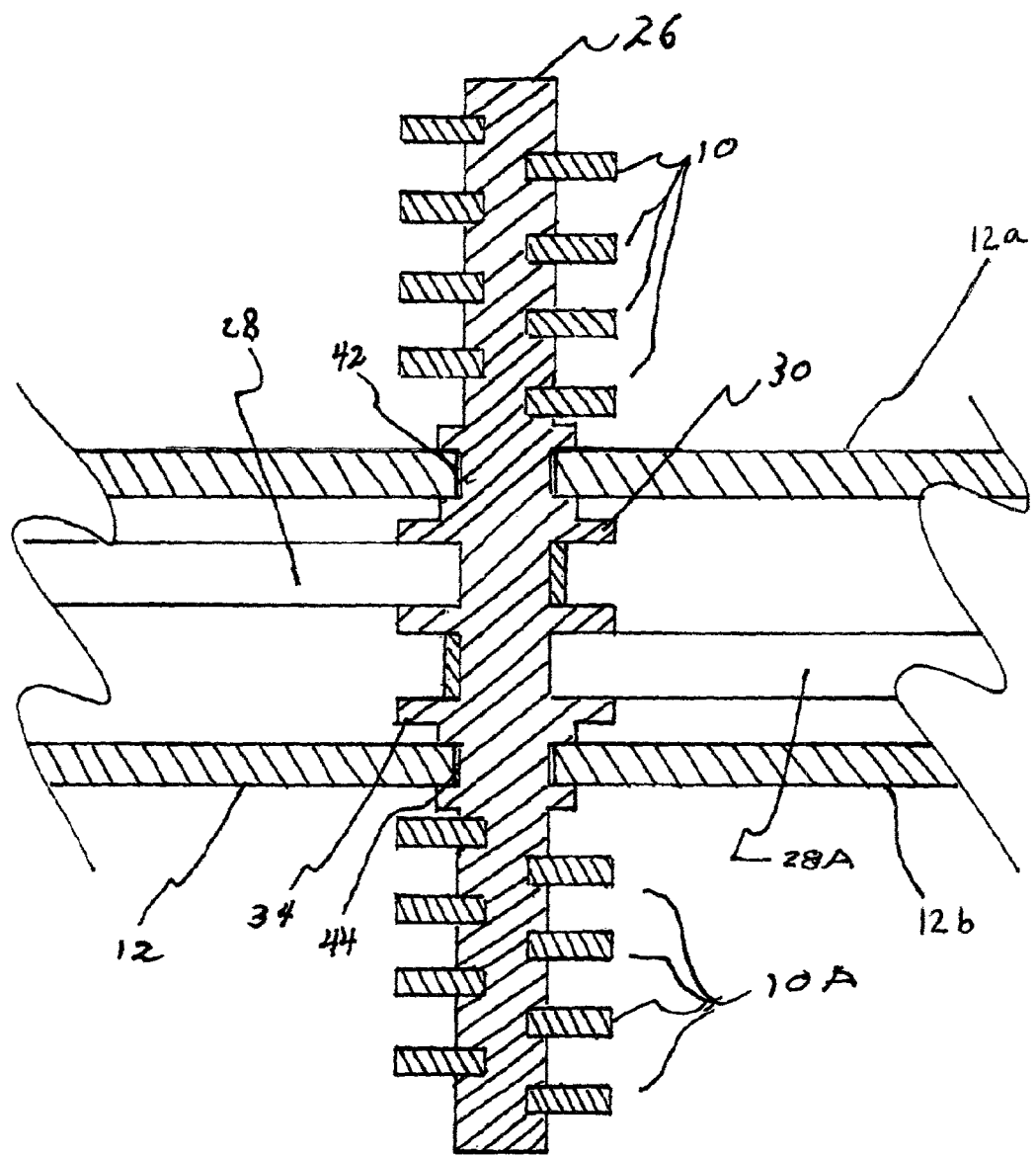
FIG. 3 is a section view of the brush spindle of the invention.
Figure 4:
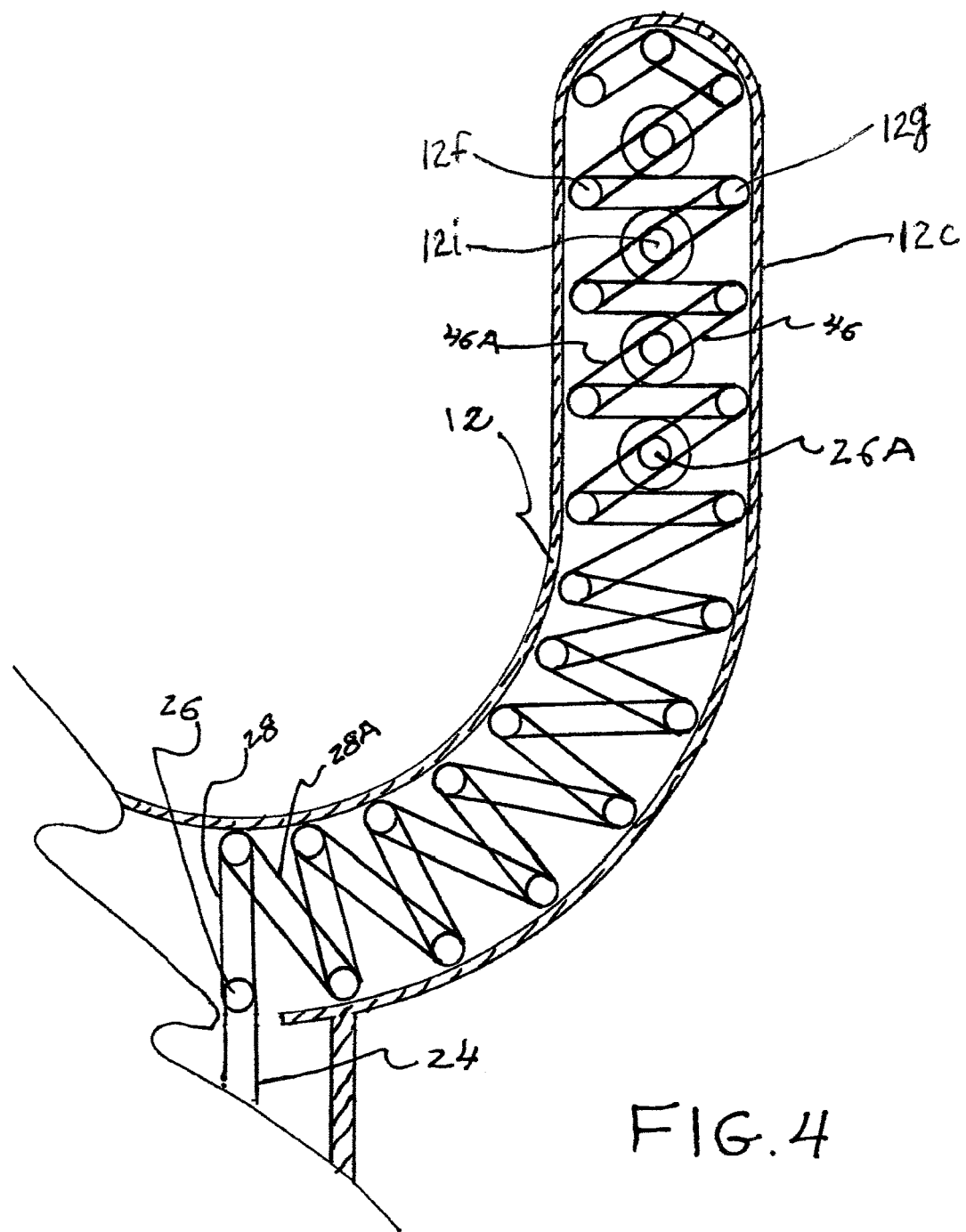
FIG. 4 is a partial section view of the U shaped brush holding portion.

FIGS. 2, 3 and 4 shows the U-shaped housing 12 in more detail. As shown in FIG, 2, the U-shaped housing 12 includes opposite leg sections 12e connected by a bite section 12d. As shown in FIG. 3, the U-shaped housing 12 includes top planar surface 12a and bottom planar surface 12b. As shown in FIG. 4 the top and bottom planar surfaces are connected by side walls 12c. As shown in FIG. 2, the toothbrush includes first and second rows 12f and 12g of brush retaining spindle shafts 26, and third and fourth rows 12i and 12h of brush retaining spindle shafts 26A disposed between the first and second rows of brush retaining spindle shafts 26, respectively.

FIG. 3 shows a section view of a single spindle 26. The belt pulleys 28, 28A are trapped within U shaped housing 12 but can rotate as the spindle passes through apertures 42, 44. The spindle 26 terminates in upper bristle head 10 and lower bristle head 10A. Belts 28, 28A transfer rotational power from one spindle to the next in a daisy chain fashion.

FIG. 4 shows the transfer of rotational power by belts 28. Shorter belts 46, 46A transfer rotational power to centrally located spindles 26A.

Figure 5:
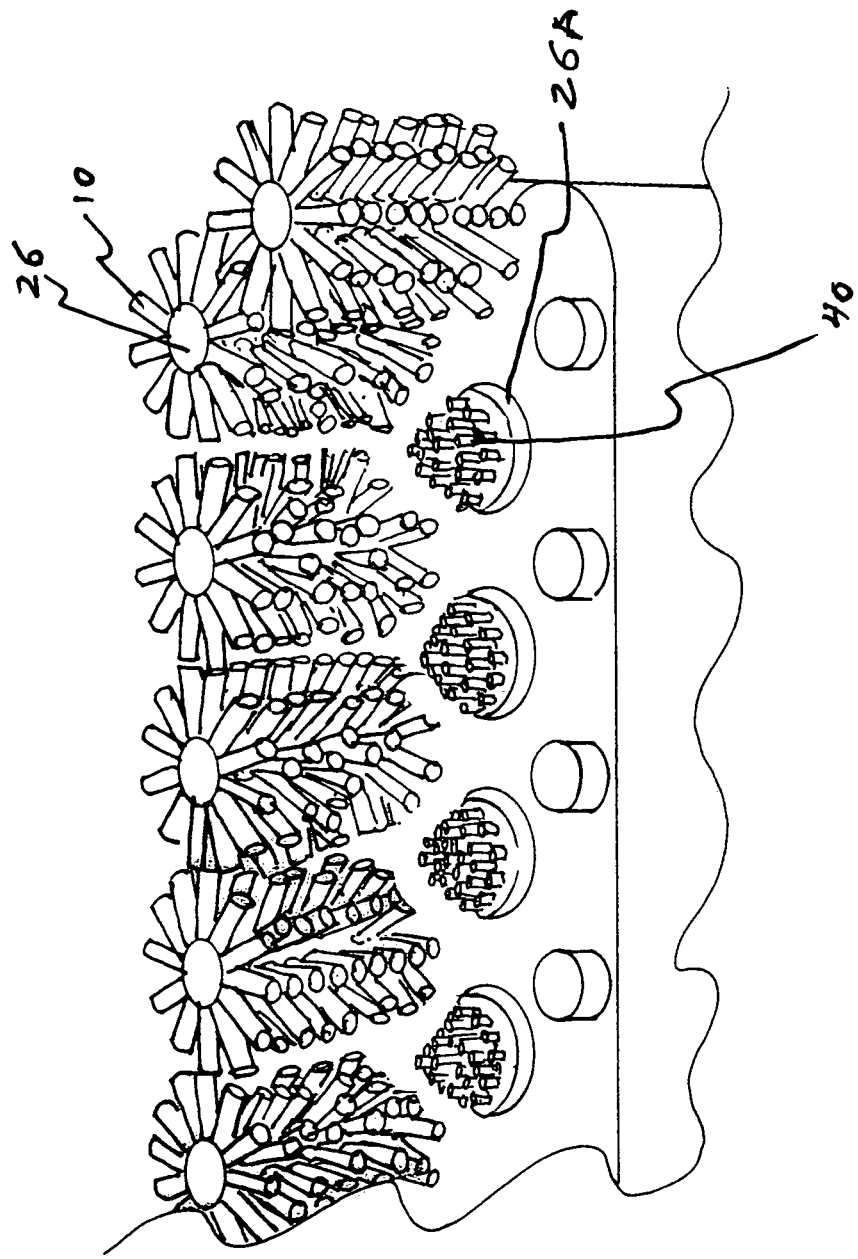
FIG. 5 is a partial perspective view of the bristle portion of the invention.

FIG. 5 shows a partial perspective view of the bristle portion 26 of the invention. The front row of bristles 10 has been removed to clearly show the low profile conical shape of the central bristles 40. These bristles are designed to brush the flat top surface portion of the user's molar teeth As can be seen by the above description and drawings, the present invention can help those with manual dexterity issues to brush all their teeth in a single action while holding onto a centrally located handle. If need be, a care giver can hold the handle for the user and insure complete brushing of all the user's teeth.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A whole mouth toothbrush comprising:
   an elongated handle portion;
   a U-shaped hollow brush retaining housing having top and bottom planar surfaces connected by side walls thereby defining a bite section and opposite leg sections;
   an electric motor with a motor shaft mounted within said hollow handle portion;
   a battery power supply mounted within said hollow handle portion;
   a microprocessor mounted within said hollow handle portion;
   a printed circuit board mounted within said hollow handle portion;
   an on-off switch mounted within said hollow handle portion;
   a primary drive belt;
   a plurality of secondary drive belts;
   a plurality of upper and lower brush heads;
   a plurality of brush retaining spindle shafts;
   said plurality of brush retaining spindle shafts comprising first and second rows of said brush retaining spindle shafts having said upper and lower brush heads mounted thereon, respectively, and disposed along said bite and leg sections for the purpose of cleaning the side portions of a user's teeth;
   said plurality of brush retaining spindle shafts further comprising third and fourth rows of said brush retaining spindle shafts having said upper and lower brush heads mounted thereon and disposed between said first and second rows and along said opposite leg sections for the purpose of cleaning the top molar portions of a user's teeth;
   said brush retaining spindle shafts also having a fixedly and centrally located first and second belt retaining pulleys disposed within said U-shaped hollow brush retaining housing;
   said motor, said battery power supply, said microprocessor, said printed circuit board and said primary drive belt all housed within said hollow handle portion;
   said primary drive belt rotatably attached to said motor shaft on one end and to a first pulley of one of said brush retaining spindle shafts on the opposite end;
   said first, second, third and fourth rows of spindle shafts each exiting upper and lower apertures located in said top and bottom surfaces of said U-shaped hollow brush retaining housing and disposed perpendicular to said top and bottom surfaces;

said brush heads fixedly attached to the upper and lower ends of said spindle shafts;

said first row of said brush retaining spindle shafts and attached brush heads mounted near the outer perimeter of said U-shaped hollow housing for the purpose of cleaning the outside surfaces of a user's teeth, said second row of said brush retaining spindle shafts and attached brush heads mounted near the inner perimeter of said U-shaped hollow housing for the purpose of cleaning the inside surfaces of a user's teeth;

said third and fourth rows of said brush retaining spindle shafts and attached brush heads mounted between said first and second rows of brush retaining spindle shafts and attached brush heads and along said leg sections of said U-shaped hollow housing for the purpose of cleaning the flat molar surfaces of a user's teeth;

said secondary drive belts rotatably attached at one end to the first belt retaining pulley of said first brush retaining spindle and the remaining secondary drive belts attached in a daisy chain fashion from the second belt retaining pulley of said first brush retaining spindle to the remaining said spindle pulleys such that when said first pulley spindle is caused to rotate, all remaining pulley spindles also rotate;

said U-shaped hollow brush retaining housing also including upwardly and downwardly extending walls attached to the outer perimeter thereof for protecting the user's cheeks from said rotating brushes;

said on-off switch having an actuation button protruding from an aperture located in said elongated handle portion;

said battery power supply providing power to said motor when said on-off switch is pressed;

said microprocessor programmed to cause said brush retaining shafts to cycle back and forth from clockwise to counter-clockwise rotation.

2. A whole mouth toothbrush as claimed in claim 1, wherein said belts are formed as miniature timing belts and said spindle shaft pulleys have mating timing belt architecture.

3. A whole mouth toothbrush comprising:

a U-shaped hollow brush retaining housing having a longitudinal axis therethrough and having top and bottom planar surfaces extending parallel to said longitudinal axis and connected by side walls thereby defining a bite section and opposite leg sections;

an elongated hollow handle portion extending from said bite section of said U-shaped hollow housing;

first and second parallel rows of brush retaining spindle shafts having upper and lower ends with brush heads mounted thereon, respectively, and disposed along said bite and leg sections for the purpose of cleaning the side portions of a user's teeth;

said first row of said brush retaining spindle shafts and attached brush heads mounted near the outer perimeter of said U-shaped hollow housing for the purpose of cleaning the outside surfaces of a user's teeth, said second row of said brush retaining spindle shafts and attached brush heads mounted near the inner perimeter of said U-shaped hollow housing for the purpose of cleaning the inside surfaces of a user's teeth;

said first and second rows of spindle shafts each exiting upper and lower apertures located in said top and bottom surfaces of said U-shaped hollow brush retaining housing and disposed perpendicular to said top and bottom surfaces;

a drive mechanism mounted within said hollow handle portion and operatively connected to said spindle shafts for rotating said spindle shafts;

whereby a user would be able to brush upper and lower dentures simultaneously without reciprocating movement of said whole mouth toothbrush.

4. A whole mouth toothbrush as claimed in claim 3, further comprising: third and fourth rows of said brush retaining spindle shafts having upper and lower ends with brush heads mounted thereon, respectively, said third and fourth rows of spindle shafts each exiting upper and lower apertures located in said top and bottom surfaces of said U-shaped hollow brush retaining housing and disposed perpendicular to said top and bottom surfaces; said thirds and fourth rows of said brush retaining spindle shafts and attached brush heads disposed along said leg sections of said U-shaped hollow housing for the purpose of cleaning the flat molar surfaces of a user's teeth; said third and fourth rows of spindles shafts operably connected to said first and second rows for rotating therewith.

5. A whole mouth toothbrush as claimed in claim 3, wherein said drive mechanism comprises an electric motor with a motor shaft mounted within said hollow handle portion; a battery power supply mounted within said hollow handle portion; a microprocessor mounted within said hollow handle portion; a printed circuit board mounted within said hollow handle portion; an on-off switch mounted within said hollow handle portion.

6. A whole mouth toothbrush as claimed in claim 5, wherein said drive mechanism further comprises said first, second, third and fourth rows of brush retaining spindle shafts having a fixedly and centrally located first and second belt retaining pulleys disposed within said U-shaped hollow brush retaining housing; a primary drive belt; a plurality of secondary drive belts; said primary drive belt rotatably attached to said motor shaft on one end and to a first pulley of one of said brush retaining spindle shafts on the opposite end; and the remaining secondary drive belts attached in a daisy chain fashion from the second belt retaining pulley of said first brush retaining spindle to the remaining said spindle pulleys such that when said first pulley spindle is caused to rotate, all remaining pulley spindles also rotate.

7. A whole mouth toothbrush as claimed in claim 6, further comprising:

said on-off switch having an actuation button protruding from an aperture located in said elongated handle portion;

said battery power supply providing power to said motor when said on-off switch is pressed; and said microprocessor programmed to cause said brush retaining shafts to cycle back and forth from clockwise to counter-clockwise rotation.

8. A whole mouth toothbrush as claimed in claim 3, wherein said belts are formed as miniature timing belts and said spindle shaft pulleys have mating timing belt architecture.

9. A whole mouth toothbrush as claimed in claim 5, further comprising:

said on-off switch having an actuation button protruding from an aperture located in said elongated handle portion;

said battery power supply providing power to said motor when said on-off switch is pressed; and said microprocessor programmed to cause said brush retaining shafts to cycle back and forth from clockwise to counter-clockwise rotation.

10. A whole mouth toothbrush as claimed in claim 6, wherein said U-shaped hollow brush retaining housing also including upwardly and downwardly extending walls attached to the outer perimeter thereof for protecting the user's cheeks from said rotating brushes.

* * * * *